United States Patent [19]

Payack et al.

[11] Patent Number: 5,274,096
[45] Date of Patent: Dec. 28, 1993

[54] HYDRAZINE SYNTHESIS

[75] Inventors: Joseph F. Payack, Somerset; Dalian Zhao, Scotch Plains, both of N.J.

[73] Assignee: Merck & Co., Inc., Rahway, N.J.

[21] Appl. No.: 852,593

[22] Filed: Mar. 17, 1992

[51] Int. Cl.$^5$ ............................................. C07D 215/12
[52] U.S. Cl. ...................................................... 546/176
[58] Field of Search ........................................ 546/176

[56] References Cited

FOREIGN PATENT DOCUMENTS

| | | |
|---|---|---|
| 0419049 | 3/1991 | European Pat. Off. . |
| 468785 | 1/1992 | European Pat. Off. . |
| WO92/03132 | 3/1992 | PCT Int'l Appl. . |

OTHER PUBLICATIONS

Jeromin et al., Chem. Ber., 120, 649–651 (1987).

*Primary Examiner*—C. Warren Ivy
*Assistant Examiner*—Raymond Covington
*Attorney, Agent, or Firm*—Mark R. Daniel; Joseph F. DiPrima

[57] ABSTRACT

An improved synthesis is described for producing a quinolinylmethoxyphenyl hydrazine which is an intermediate in the preparation of quinolinylmethoxyindoles useful as inhibitors of leukotriene biosynthesis. The improved process eliminates two isolation steps and yields a product of high purity.

4 Claims, No Drawings

HYDRAZINE SYNTHESIS

BACKGROUND OF THE INVENTION

EP 419,049 describes a process for synthesizing 1-(p-chlorobenzyl)-1-[4-(quinolin-2-ylmethoxy)phenyl)hydrazine via a multi-step procedure requiring isolations of toxic compounds. This hydrazine is an intermediate in the production of (quinolinylmethoxy)indoles disclosed in EP 419,049 which are inhibitors of leukotriene biosynthesis.

SUMMARY OF THE INVENTION

The invention is an improved and streamlined process for the preparation of a (quinolinylmethoxy)phenyl hydrazine compound, which eliminates two isolation steps and yields a high purity hydrazine.

DETAILED DESCRIPTION

The process comprises:
1) reacting 2-methylquinoline with trichloroisocyanuric acid dissolved in acetonitrile;
2) reacting the 2-chloromethylquinoline product of step (1) in acetonitrile with 4-acetamidophenol and potassium carbonate;
3) hydrolyzing the N-acetyl-4-quinolin-2-ylmethoxy)aniline product of step (2) in ethanol with KOH;
4) reacting the 4-(quinolin-2-ylmethoxy)aniline product of step (3) in water, first with sodium nitrite/HCl then with sodium dithionite/NaOH, and finally adding methanol thereto; and
5) reacting the 4-(quinolin-2-ylmethoxy)phenylhydrazine product of step (4) with p-chlorobenzyl chloride, tetrabutylammonium bromide and diisopropylethylamine to yield 1-(p-chlorobenzyl)-1-[4-(quinolin-2-ylmethoxy)phenyl]hydrazine.

Referring to the above synthesis, step (1) is run at about 0° C. and uses about 40 mol % trichloroisocyanuric acid, i.e. 120 mol % chlorine. The reaction takes about 18 hours, after which excess and spent trichlorocyanuric acid is filtered out and the chloroquinaldine solution is used directly in the alkylation step, thus eliminating the need to isolate the product.

Alkylation, step (2), uses about 100 mol % phenol and 115 mol % carbonate and takes 20-24 hours at reflux temperature. The carbonate is added in the form of a 325 mesh powder. Following alkylation the aniline product crystallizes from the acetonitrile solvent at about 0° C. and can then be washed in $H_2O$ to remove excess carbonate. Advantageously, steps (1) and (2) eliminate the need for extraction of the chlorinated product of step (1) and all solvent evaporations.

The chlorination of quinaldine using trichloroisocyanuric acid has been described by G. E. Jeromin et al, Chem. Ber., 120, 649-651 (1987). The process uses chloroform as the solvent, requires tedious work-up and purification steps, and gives a product in 53% yield. The use of chlorinated solvents such as chloroform or carbon tetrachloride is typical of chlorination reactions. In contrast, the present invention uses acetonitrile for the chlorination step which is advantageously also used in step (2), and which results in an overall yield for step (1) of 76% as compared to a yield of only 53% for step (1) as described in Jeromin et al.

The hydrolysis, step (3), is run in ethanol, using 10N KOH at reflux for 41 hours. The ethanol is then removed, $H_2O$ added, and the aniline product isolated at about 10° C.

As with steps (1) and (2), steps (4) and (5) are combined and require no isolation of the intermediate hydrazine 5, a toxic compound which is unstable in air. In step (4), the aniline of step (3) is diazotized with 105 mol % sodium nitrite at low pH. The resultant diazonium salt is then reduced with 300 mol % sodium dithionite. Following reduction, excess dithionite is removed by aging at low pH and methanol (1.3:1 v/v) is added to the resultant hydrazine slurry. Advantageously, the water/alcohol solvent system eliminates the need for additional solvents in step (5) such as $CH_2Cl_2$, described in EP 419,049. The final alkylation uses 400 mol % p-chlorobenzyl chloride in neutral pH, at 35° C. for 3 hours. Following removal of organic and inorganic impurities with $H_2O$, THF and MeOH washes, the final product is isolated in 96-99% purity at about 0° C.

The hydrazine can be used as described in Example 1A, step E of EP 419,049.

The invention is further defined by reference to the example, which is intended to be illustrative and not limiting.

EXAMPLE 1

1-(p-Chlorobenzyl)-1-[4-(quinolin-2-ylmethoxy)-phenyl]hydrazine

Step 1: Chlorination

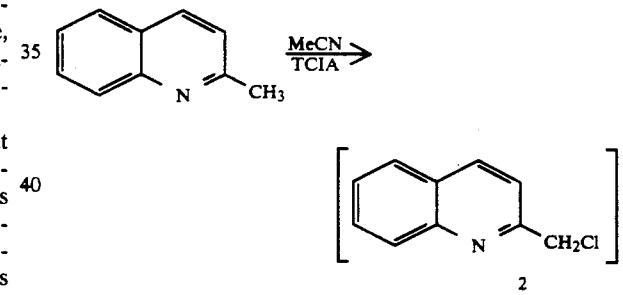

A 1 L, 3-neck flask equipped with a mechanical stirrer, addition funnel and a thermocouple was purged with nitrogen. Quinaldine (30.0 g) (Aldrich) and MeCN (230 mL) (EM) were charged to the flask and the solution was chilled to −5° C. Trichloroisocyanuric acid (19.5 g) (Aldrich) dissolved in MeCN (65 mL+5 mL wash) was added over 40 min., maintaining the temperature between −5° C. and 0° C. The white suspension was stirred at 0° C., excluding light for 20-24 hrs. The mixture was then assayed, filtered into a tared 1 L 3-neck flask and the filtercake washed with MeCN (10 mL).

HPLC: Zorbax RX $C_8$, 25 cm × 4.6 mm; eluent: water (0.1% $H_3PO_4$)/$CH_3CN$ 40/60; flow rate=1.5 mL/min; UV detection at 250 nm; sample concentration=4 drops diluted to 25 mL; retention time 3.39 min; 76 area %.

Step 2: Alkylation

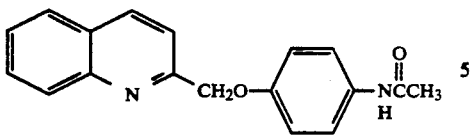

3

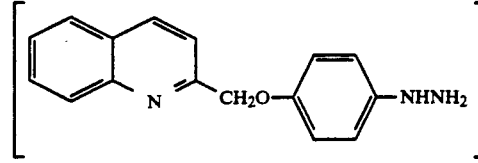

5

4-Acetamidophenol (23.4 g, 100 mol %) (Aldrich) and K₂CO₃ (24.5 g, 115 mol %) (Aldrich, powdered, 325 mesh) were charged to the flask of Step 1. The mixture was refluxed 20-24 hrs, then chilled over ½ hr to 0° C. After a 1 hr age at 0° C., the mixture was filtered and the filtercake was washed with 0° C. acetonitrile (60 mL, 60 mL and 40 mL), then was pulled dry on a fritted funnel. The damp cake was then charged to a 500 mL flask and was mechanically stirred for 2 hrs with water (250 mL). The material was collected by filtration and the filtercake washed with water (2×75 mL). The solid was dried in vacuo at 45° C. to give 35.4 g (57% from quinaldine) of 3 as a tan solid, 98 area and weight percent purity.

HPLC: Zorbax RX C₈, 25 cm×4.6 mm; eluent=water (0.1% H₃PO₄)/CH₃CN 50/50, 1.5 mL/min; UV detection at 250 nm; sample concentration=4 drops diluted to 25 mL; retention time 2.31 min; 98 area %.

Step 3: Hydrolysis

3 $\xrightarrow{\text{KOH}}_{\text{EtOH}}$

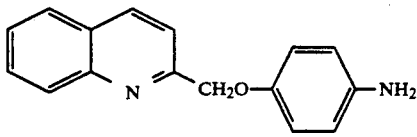

4

A 1-liter, 3-neck flask equipped with a mechanical stirrer and reflux condenser was purged with nitrogen. Acetamide 3 (72.6 g), ethanol (370 mL) and 10N KOH (79.5 mL) were charged to the flask and the mixture was heated at reflux for 41 hrs. 216 mL ethanol was removed via distillation (1 atm) and the product was crystallized by the addition of water (160 mL). The brown suspension was chilled to 10° C. and aged 1 hr, then was filtered and the filtercake washed with water (4×40 mL). The material was dried in vacuo at 60° C. to give 57.7 g (93%) of a brown solid.

HPLC: Zorbax RX C₈, 25 cm×4.6 mm; eluent=water (0.1% H₃PO₄)/CH₃CN 50/50, flow rate=1.5 mL/min; UV detection at 250 nm; sample concentration=0.2 mg/mL; retention time 1.41 min; 96 area %.

Step 4: Diazotization/Reduction

4 $\xrightarrow[\text{2) Na}_2\text{S}_2\text{O}_4]{\text{1) NaNO}_2,\text{ HCl}}$ A 1-liter 3-neck flask equipped with a mechanical stirrer, thermocouple, and pH probe was charged with water (250 mL) and chilled to 0° C. The flask and water were degassed with nitrogen by a combination of 3 evacuate/fill cycles and sparging (15 min). 5N NaOH (8.0 mL washed in with 3 mL H₂O) was added followed by sodium dithionite (46.4 g).

A 250 mL, 3-neck flask equipped with a mechanical stirrer and thermocouple was purged with nitrogen, then water (40 mL) and aniline 4 (20.0 g) was charged. The slurry was chilled to 0° C., and 12N HCl (20 mL) was added over 30 min, with the temperature maintained below 15° C. The slurry was chilled to 0° C., then a solution of sodium nitrite (5.8 g) in water (15 mL) was added over 30 min, maintaining the temperature between 0° to 5° C. The nitrite solution was washed in with water (5 mL). The brown solution was aged 1 hr at 0° C. The solution was then transferred (within 15 min, 0°-7° C.) via cannula to the above dithionite solution, maintained at 0° C. The diazonium solution was washed over with 7 mL H₂O. A thick white suspension resulted. The mixture was warmed to 23°-25° C. and aged for 1 hr (pH dropped below 4, decomposing the excess dithionite and turning the suspension pink), then assayed for hydrazine 5.

HPLC Gradient Assay: Aq=0.01M heptane sulfonic acid sodium salt in 0.1% H₃PO₄; eluent=65/35 Aq/MeCN 0 min, ramp to 30/70 Aq/MeCN over 10 min, hold 30/70 Aq/MeCN for 5 min. Flow rate=1.5 mL/min, sample concentration=3 drops diluted to 25 mL with 50/50 Aq/MeCN; UV detection at 250 nm; retention time: 2.8 min.

Step 5: Alkylation

[5] $\xrightarrow[\text{MeOH/Water}]{\substack{\text{Bu}_4\text{NBr}\\ \text{4-ClC}_6\text{H}_4\text{CH}_2\text{Cl}\\ \text{(i-Pr)}_2\text{NEt}}}$

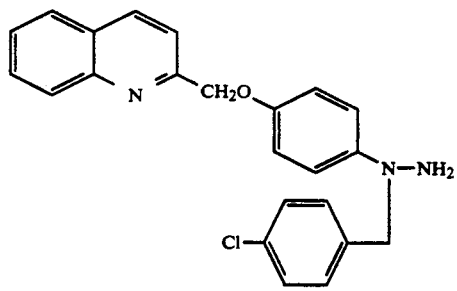

The mixture from Step 4 was chilled to 10°-15° C. and 5N NaOH (30 mL washed in with 3 mL H₂O) was added over 10 min keeping the temperature below 25° C. i-Pr₂NEt (56 mL) (Aldrich) was added, washed in with 5 mL MeOH keeping the temperature below 25° C. Tetrabutylammonium bromide (7.4 g) (Aldrich) followed by methanol (360 mL) was charged, maintaining the temperature below 25° C. The mixture was then warmed to 25° C. and a solution of p-chlorobenzyl chloride (51.5 g) (Aldrich) in methanol (50 mL) was added over 1 hr while warming the reaction to 35°-37° C. The p-chlorobenzyl chloride was washed in with 10 mL methanol. The white suspension was aged at 35°-37° C. for 3 hrs then was assayed and filtered warm. The filtercake was washed: 1:1 MeOH:H$_2$O, 200 mL; H$_2$O, 3×200 mL; 1:1 MeOH:H$_2$O, 200 mL; and MeOH, 3×100 mL. The slightly yellow solid was dried in vacuo at 25° C. (30° C. maximum) to give 24.7 g, 95 wt %, of the title product.

Isocratic HPLC Assay: Aq=0.01M heptane sulfonic acid sodium salt in 0.1% H$_3$PO$_4$); eluent=40/60 Aq/MeCN; flow rate=1.5 mL/min; UV detection at 250 nm; retention time: 2.5 min; 94 area %.

What is claimed is:

1. An improved process for preparing 1-(p-chlorobenzyl)-1-[4-(quinolin-2-ylmethoxy)phenyl]hydrazine which comprises:

1) reacting 2-methylquinoline with trichloroisocyanuric acid dissolved in acetonitrile;
2) reacting the 2-chloromethylquinoline product of step (1) in acetonitrile with 4-acetamidophenol and potassium carbonate;
3) hydrolyzing the N-acetyl-4-quinolin-2-ylmethoxy)aniline product of step (2) in ethanol with KOH;
4) reacting the 4-(quinolin-2-ylmethoxy)aniline product of step (3) in water, first with sodium nitrite/HCl then with sodium dithionite/NaOH, and finally adding methanol thereto; and
5) reacting the 4-(quinolin-2-ylmethoxy)phenylhydrazine product of step (4) with p-chlorobenzyl chloride, tetrabutylammonium bromide and diisopropyl ethyl amine to yield 1-(p-chlorobenzyl)-1-[4(quinolin-2-ylmethoxy)phenyl]hydrazine.

2. In a process for preparing 1-(p-chlorobenzyl)-1-[4-(quinolin-2-ylmethoxy)phenyl]hydrazine which comprises:

1) reacting 2-methylquinoline with trichloroisocyanuric acid;
2) reacting the 2-chloromethylquinoline product of step (1) with 4-acetamidophenol and potassium carbonate;
3) hydrolyzing the N-acetyl-4-quinolin-2-ylmethoxy)analine product of step (2) in ethanol with KOH;
4) reacting the 4-(quinolin-3-ylmethoxy)aniline product of step (3) in water, first with sodium nitrite/HCl, then with sodium dithionite/NaOH; and
5) reacting the 4-(quinolin-2-ylmethoxy)phenylhydrazine product of step (4) with p-chlorobenzyl chloride, tetrabutylammonium bromide and diisopropyl ethyl amine to yield 1-(p-chlorobenzyl)-1-[4-(quinolin-2-ylmethoxy)phenyl]hydrazine;

the improvements which comprise:

1) in said step (1) reacting the 2-methylquinoline with trichloroisocyanuric acid dissolved in acetonitrile;
2) reacting the 2-chloromethylquinoline product of said step (1) in acetonitrile with 4-acetamidophenol and potassium carbonate;
3) adding methanol at the end of said step (4); and
4) in said step (5) reacting the 4-(quinolin-2-ylmethoxy)phenylhydrazine product of said step (4) in H$_2$O/methanol with p-chlorobenzyl chloride, tetrabutylammonium bromide and diisopropyl ethyl amine to yield 1-(p-chlorobenzyl)-1-[4(quinolin-2-ylmethoxy)phenyl]hydrazine;

3. A process of claim 2 wherein the improvements comprise;

1) in said step (1) reacting the 2-methylquinoline with trichloroisocyanuric acid dissolved in acetonitrile; and
2) reacting the 2-chloromethylquinoline product of said step (1) in acetonitrile with 4-acetamidophenol and potassium carbonate.

4. A process of claim 2 wherein the improvements comprise:

1) adding methanol at the end of said step (4); and
2) in said step (5) reacting the 4-(quinolin-2-ylmethoxy)phenylhydrazine product of said step (4) in H$_2$O/methanol with p-chlorobenzyl chloride, tetrabutylammonium bromide and diisopropyl ethyl amine to yield 1-(p-chlorobenzyl)-1-[4(quinolin-2-ylmethoxy)phenyl]hydrazine.

* * * * *